United States Patent
Fleishman

(10) Patent No.: US 11,039,226 B2
(45) Date of Patent: Jun. 15, 2021

(54) SYSTEM AND METHOD FOR CONSTANT ONLINE WATER QUALITY AND SAFETY MONITORING OF A FLUID SYSTEM

(71) Applicant: CYWAT TECHNOLOGIES LTD., Bnei Brack (IL)

(72) Inventor: David Fleishman, Bnei Brack (IL)

( * ) Notice: Subject to any disclaimer, the term of this patent is extended or adjusted under 35 U.S.C. 154(b) by 0 days.

(21) Appl. No.: 16/336,122

(22) PCT Filed: Oct. 1, 2017

(86) PCT No.: PCT/IL2017/051111
§ 371 (c)(1),
(2) Date: Mar. 25, 2019

(87) PCT Pub. No.: WO2018/061015
PCT Pub. Date: Apr. 5, 2018

(65) Prior Publication Data
US 2019/0297397 A1 Sep. 26, 2019

Related U.S. Application Data

(60) Provisional application No. 62/401,218, filed on Sep. 29, 2016.

(51) Int. Cl.
*H04Q 9/00* (2006.01)
*H04W 4/38* (2018.01)
*G01N 33/18* (2006.01)
*G08B 21/18* (2006.01)

(52) U.S. Cl.
CPC .............. *H04Q 9/00* (2013.01); *G01N 33/18* (2013.01); *G08B 21/18* (2013.01); *H04W 4/38* (2018.02); *H04Q 2209/40* (2013.01)

(58) Field of Classification Search
CPC ....... H04Q 9/00; H04Q 2209/40; H04W 4/38; G01N 33/18; G08B 21/18
See application file for complete search history.

(56) References Cited

U.S. PATENT DOCUMENTS

| | | |
|---|---|---|
| 6,245,224 B1 | 6/2001 | Enoki et al. |
| 7,136,762 B2 | 11/2006 | Sam et al. |
| 7,289,923 B2 | 10/2007 | Marovitz |
| 2006/0020427 A1 | 1/2006 | Kahn et al. |
| 2006/0031040 A1 | 2/2006 | Wolfe |

(Continued)

FOREIGN PATENT DOCUMENTS

| | | |
|---|---|---|
| CN | 103245378 | 8/2013 |
| CN | 204462116 | 7/2015 |

(Continued)

*Primary Examiner* — Amine Benlagsir

(57) ABSTRACT

A method for monitoring water quality in a water supply network, the method including: providing a plurality of sensor units at predefined locations along the water supply network; monitoring water in the water supply network with the sensor units to receive detected sensor values; communicating the detected sensor values from the plurality of sensor units to a computer server in real-time; analyzing the sensor values at the computer server in order to detect changes in quality of water moving between the sensor units; and outputting real-time data from the computer server to a geographic information system (GIS) user interface or a Graphic User Interface (GUI).

18 Claims, 11 Drawing Sheets

(56) References Cited

U.S. PATENT DOCUMENTS

| | | | |
|---|---|---|---|
| 2007/0090059 A1 | 4/2007 | Plummer et al. | |
| 2008/0109175 A1* | 5/2008 | Michalak | C02F 1/008 |
| | | | 702/50 |
| 2011/0215945 A1* | 9/2011 | Peleg | G01M 3/2807 |
| | | | 340/870.02 |
| 2012/0125771 A1* | 5/2012 | Salzer | G01N 27/308 |
| | | | 204/412 |
| 2012/0170025 A1 | 7/2012 | Cros et al. | |
| 2012/0228235 A1* | 9/2012 | Mehta | C02F 1/004 |
| | | | 210/748.11 |
| 2013/0332090 A1 | 12/2013 | Scolnicov et al. | |
| 2014/0152465 A1 | 6/2014 | Yeh et al. | |
| 2014/0163925 A1 | 6/2014 | Wolfe | |
| 2014/0172322 A1 | 6/2014 | Wolfe | |
| 2015/0310634 A1 | 10/2015 | Babcock et al. | |
| 2016/0202228 A1* | 7/2016 | Ba | G01N 33/18 |
| | | | 702/50 |
| 2016/0306366 A1* | 10/2016 | Yokokawa | F17D 3/00 |
| 2017/0305759 A1* | 10/2017 | Braun | C02F 1/008 |

FOREIGN PATENT DOCUMENTS

| | | |
|---|---|---|
| JP | H08178818 | 7/1996 |
| WO | 2010076558 | 10/2010 |
| WO | 2014207322 | 12/2014 |

\* cited by examiner

Cross reference between all Sensor Units

Cross reference with Main Sensor Unit

SYSTEM AND METHOD FOR CONSTANT ONLINE WATER QUALITY AND SAFETY MONITORING OF A FLUID SYSTEM

FIELD OF THE INVENTION

The present invention relates to a platform and system for monitoring water and other fluid sources for quality and safety purposes and, more particularly, to an online, real-time cloud-based system that receives monitoring data from field units and cross references the monitoring data as well as performing data analysis using artificial intelligence (AI) software and algorithms. The system identifies the water source and monitoring units are spread throughout the entire water system or other fluid system.

BACKGROUND OF THE INVENTION

Introduction of harmful agents such as biological or chemical agents, or other events occurring in important infrastructure resources such as the national or municipal water supply can be a catastrophic event, even if it is a non-deliberate one.

Water constitutes a national resource and source of life and growth. At the same time, potentially grave harm and significant damage can be caused to water sources by hostile elements and sanitation-related incidents alike.

In recent years and in light of the events that occurred all over the world, the security organizations reached a unified conclusion that it is very likely that terror groups will target and strike at national infrastructure facilities in heavily populated areas using the population's own infrastructure systems and way of life in order to cause as much damage as possible.

Unfortunately, the common design of water infrastructure system the world over—a supply grid that looks like as a tree with many branches and sub branches—ensures that harmful water-borne agents can be spread to even the most remote houses on the outskirts of the cities and suburbs. Additionally, not all threats come from terrorists. Employee incompetence or malfunctioning equipment can create the opportunity for an unintentional, but deadly, water contamination event.

Furthermore, natural disasters such as earthquakes, tornadoes and hurricanes, and well as unintentional work accidents that occur during mining or drilling, for example, can damage a pipeline containing drinking water. Such occurrences can cause bacteria and pollutants to penetrate the water system and cause widespread illness.

Urban monitoring systems today, are using—believe it or not—manual tests that are carried out at a limited number of locations throughout the cities, when, in a town of 10,000 inhabitants, only 6 or 7 random water samples are taken to test water quality once a week! And the results are received only after 24 to 48 hours.

Installing systems for monitoring water quality all over the city is practically an unachievable goal due to manpower constraints, low maintenance capabilities and the cost of the current systems. Therefore, very little is done in smaller regions and only large national bodies can run and maintain big water quality monitoring stations.

Current monitoring system installations paint a sad and unreliable picture; the equipment is very big and expensive to purchase, the systems are unstable and require skilled personnel to operate and perform regular maintenance, both of which are costly. The systems need to be regularly calibrated and use large amounts of expensive chemicals.

Furthermore, there are two ways of monitoring free chlorine, which is one of the values to be checked, and both ways are problematic. One method is colorimetric analysis which includes the introduction of expensive reagents into the water. The water cannot be reintroduced into the water system after testing.

The other method is amperometric measurement where the standard amperometric sensor design consists of two electrodes (anode and cathode) that measure a change in current caused by the chemical reduction of hypochlorous acid at the cathode. The current that flows because of this reduction is proportional to the chlorine concentration. A membrane and electrolyte help to control the reaction. Flow rate and pressure must be carefully controlled for accurate measurement. This method entails a great deal of calibration during regular use and needs to be recalibrated for each new water source. Today, water sources for any given water system change quite regularly, compounding the drawbacks of this method.

In tests conducted on existing systems in recent years, experts looked for a simple, low cost solution that required minimal maintenance, and sent stable, reliable data regarding the quality of the water without the need for experts to analyze the results. No systems were found that met these criteria.

SUMMARY OF THE INVENTION

The immediate innovative platform is designed to meet the criteria set out by experts as discussed above. The innovative platform provides a paradigm shift away from conventional security measures aimed exclusively at protecting water facilities, to protecting both the treatment plant and the water itself, within the pipelines.

This is achieved by obtaining continuous information on the quality of water supplied to the residents all year round. This breakthrough method in this inventive platform provides a type of a "Cyber protection" or "online/real-time protection" to the water.

The platform monitors and provides continuous information on all municipal water lines and systems, requires almost zero maintenance, has remote calibration capabilities as well as having a learning AI system. The platform includes small units equipped with smart, cheap, innovative sensors and/or multi-sensor modules. The units test a number of water quality parameters and transmit the test result data to a cloud server that stores and analyzes the information obtained in the field.

By using sophisticated algorithms developed by the inventor and data mining systems that allow this platform to identify vulnerabilities and malfunctions in real time and with the utmost precision and predict the development of glitches, even at their genesis.

GIS software is used to create a web-based user interface and online display of a live, dynamic grid. The interface and display allow the system administrators to know the quality of the water in all the water lines in real time and set specific alerts for any defect or glitch detected in the water quality. A client-side application is also provided giving users (maintenance crews, analysists, administrators, supervisors etc.) the ability to monitor, track, receive notifications, alerts and more, while on the go or in the field.

This platform also gives a unique solution that addresses the problems of maintenance of the current monitoring systems, by using remote calibration and maintenance methods.

According to the present invention there is provided a method for monitoring water quality in a water supply network, the method including: providing a plurality of sensor units at predefined locations along the water supply network; monitoring water in the water supply network with the sensor units to receive detected sensor values; communicating the detected sensor values from the plurality of sensor units to a computer server in real-time; analyzing the sensor values at the computer server in order to detect changes in quality of water moving between the sensor units; and outputting real-time data from the computer server to a geographic information system (GIS) user interface or a Graphic User Interface (GUI).

According to further features in preferred embodiments of the invention described below the computer server records the detected sensor values in a storage repository and compares sensor values from each of the plurality of sensor units to recorded values of same the sensor units stored in the repository.

According to still further features in the described preferred embodiments the computer server compares communicated sensor values from sequentially located sensor units and sends alerts to the GIS user interface when a localized abnormality is determined at one or more of the sequentially located sensor units relative to other the sequentially located sensor units.

According to further features the computer server compares communicated sensor values with predefined sensor value parameters.

According to further features the method further includes sending alerts to the GIS or GUI when the communicated sensor values are outside the parameters.

According to further features the server computer learns to adjust the parameters when the alerts are false.

According to further features the plurality of sensor units comprises a main unit and sub-units and the predefined sensor value parameters are calibrated according to sensor values detected at the main sensor unit.

According to further features the sensor units comprise passive sensors only or passive and active sensors.

According to further features the outputting includes sending notifications of anomalies or malfunctions, including locations thereof.

According to further features the method further includes calculating an affected area based on a rate of spread of water from the locations, and effecting at least one of: sending an alert including an indication of the affected area, automatically isolating the affected area, effecting an automated purification process on water in the affected area, and flushing water in the affected area from the water supply network.

According to further features the plurality of sensor units comprises a main unit and sub-units, the main unit being located in closest proximity to a source of treated water relative to the sub-units.

According to further features the computer server compares communicated sensor values from sub-units to communicated sensor values from the main unit.

According to further features the computer server compares communicated sensor values from sub-units with at least one of: communicated sensor values from other sub-units in a same tributary; communicated sensor values from the main unit; and communicated sensor values from parallel the sub-units in nearby tributaries.

According to further features the computer server further includes a database of contamination signatures, such that detection of one of the contamination signatures results in an alert being sent to the GIS or GUI.

According to further features the contamination signatures are based on relative values between parameters of free chlorine, PH, turbidity and conductivity.

According to further features the contamination signatures are based on predefined values of at least one of: a free chlorine value, a PH value, a turbidity value and a conductivity value.

According to further features the contamination signatures are detectable over time, and wherein the recorded values are analyzed and compared to the contamination signatures, and the detection is a result of a match or a prediction of a future match.

According to further features the contamination signatures are specific to one or more profiles of water, each of the profiles relating to water from a different water source.

According to further features the analysis of the sensor values stored in the repository detects a degradation of water pipes over time.

According to further features one of the plurality of sub units is positioned at each junction or split in a pipeline along the water supply network.

According to another embodiment there is provided a monitoring system for a water supply network, the system including: a main sensor unit located at an outlet from a water source of the water supply network; a plurality of sub-units sequentially located within the water supply network; a processing facility in electronic communication with the main sensor unit and the plurality of subunits, the processing facility configured to receive sensor values communicated from the main and sub unit and the processing facility comprising a processor and non-transient memory having computer-readable instructions stored thereon instructing the processor to: compare the received sensor values from each of the sub units with the main sensor unit; compare the received sensor values from each of the sub units to a remainder of the sub units; and communicate an aggregated set of values to be displayed on a Geographical Information System (GIS) or Graphic User Interface (GUI) such that the GIS or GUI displays a visually characterization of the received sensor values.

According to further features the processor is further instructed to: store the received sensor values in a repository; compare the received sensor values from a main sensor unit or a given the sub unit with stored sensor values from the repository for same the unit; and notify is an anomalous pattern is identified by the comparison.

BRIEF DESCRIPTION OF THE DRAWINGS

Various embodiments are herein described, by way of example only, with reference to the accompanying drawings, wherein.

DESCRIPTION OF THE PREFERRED EMBODIMENTS

The principles and operation of a platform, system and method for monitoring water quality in a fluid system according to the present invention may be better understood with reference to the drawings and the accompanying description.

Figure 1:
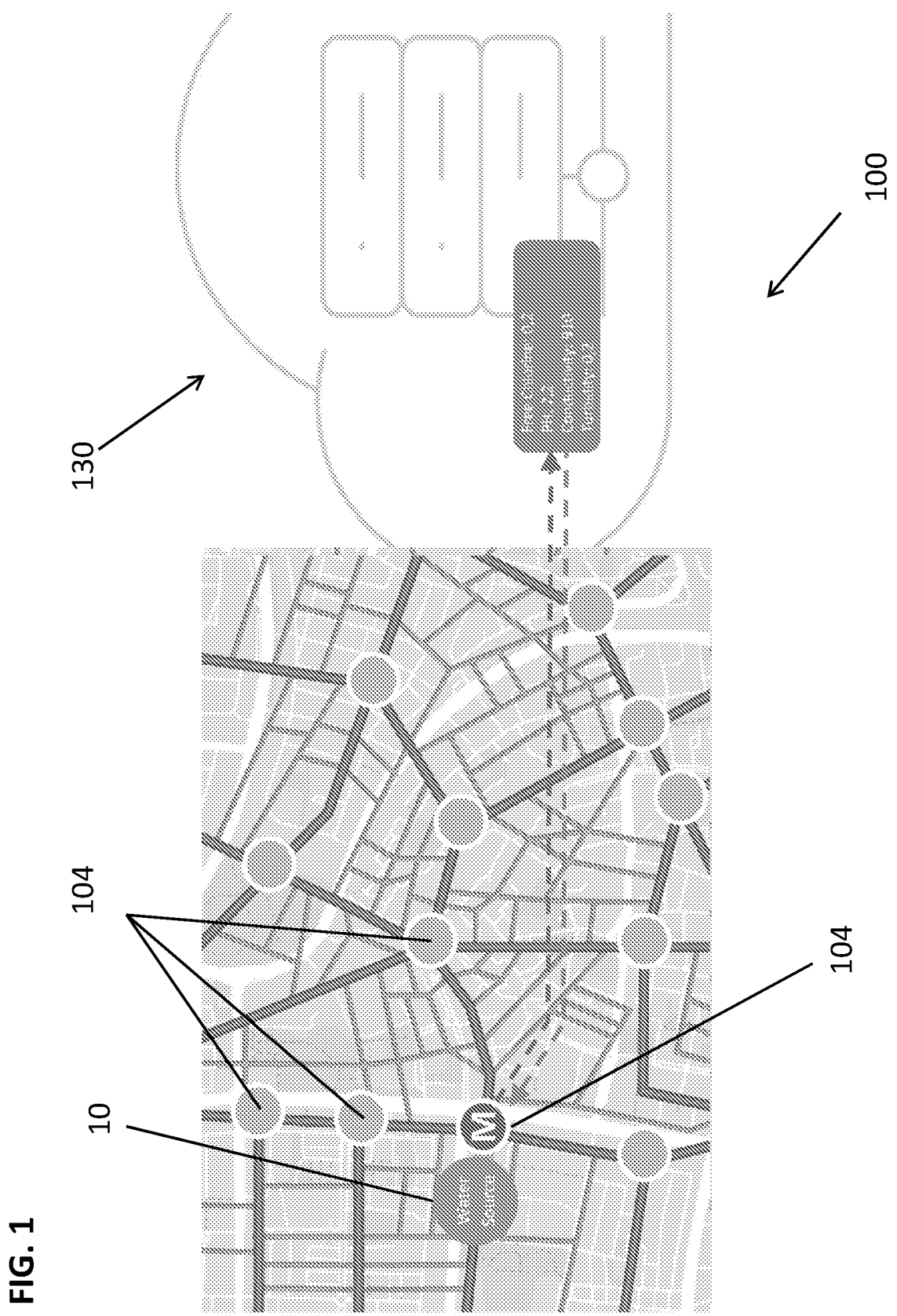
FIG. 1 is a diagrammatic depiction of the system/platform for constant, online fluid safety & quality monitoring.

Referring now to the drawings, FIG. 1 illustrates a system/platform for constant, online fluid safety & quality monitoring. The platform capabilities include: recognizing water origin; on-line, multi-level-buffer, cross-checking and data analyses on the entire spread of the water grid and pipelines; early warning capabilities in real time; early stage prediction capabilities (e.g. based on preliminary indicators, cross referencing with historical data, etc.), real-time detection and recognition of harmful agents using data analysis, AI software and algorithms via cloud based servers (cloud computing).

The present invention successfully addresses the shortcomings of the known configurations by providing a platform 100 comprising three components:

1. A number of advanced sensor modules or units spread out over a defined geographic location such as an army installation, a village, city, country etc. Each sensor unit includes a number of sensors, including electroscopic and/or electro-optic sensors that test various characteristics of water in a water system and/or other fluids. These parameters give an overall indication of the quality and health of the water or fluid. The units are installed within the water system.

For each system a main unit 102 and sub units 104 are distributed throughout the water supply network. The main unit is placed near the outlet from the treatment plant or potable water reservoir 10 (collectively and interchangeably referred to as a "water source") in order to monitor the water with the optimum health and quality just as it enters the water supply network. The sub units are installed through the fluid network. The sub units are preferably placed at each juncture in the pipe system. This configuration allows the system to cover the supply network in as complete a manner as possible and receive.

2. Server computers 130 (e.g. cloud servers) analyze raw data received from the sensor units (including comparison of parallel units along the system, comparing the units in series as well as comparing newly received data with stored/historical data for the same units). Cross referencing between the detected sensor values in at the sub units and those at the main unit, as well as between the sub units themselves, gives the operators a correct, real-time picture of the health and quality of the water in the entire supply network.

3. Display system (See FIG. 6) for showing a dynamic grid of the water system (i.e. the health of the water in the system) to the end-user.

Innovatively, sensor units installed in the water grid can be remotely calibrated (e.g. by calibrating a main unit and automatically synchronizing sub-units with the main unit which is calibrated manually). Further innovatively, in preferred embodiments, for most of the monitoring activities, the water or fluid does not need to be [permanently] removed from the water system. For those monitoring activities that do require the removal of water samples from the system, the water is unchanged during the monitoring procedures since all the monitoring activities are passive, e.g. based on electro-optic/spectrographic/spectral sensors which do not cause any reactions in the water. As such, water samples that are removed from the water system for processing, analysis and monitoring can be returned to the system afterwards. However, in some embodiments, chemical and/or electrochemical analyses are performed on water samples that are extracted from the system and then discarded.

The principles and operation of a platform and system for monitoring a fluid source and/or system according to the present invention may be better understood with reference to the drawings and the accompanying description.

A water/fluid system (hereafter reference is only made to a "water system", however it is made clear that every reference to a water system applies equally to other fluid systems such as fuel, gas, steam, sewerage systems and the like, and especially to a water supply network for providing potable water) is usually built according to a tree structure, with a central node/channel having tributaries running off the main channel. The lines connecting elements are called "branches". Nodes without children are called leaf nodes, "end-nodes", or "leaves".

The innovative platform is built into the water system according to a similar tree structure with "parent" (main unit) nodes and "child" (sub-unit) nodes. A plurality of sensor units are provided at predefined locations along the water supply network. Accordingly, a main sensor unit sits at the major water junction and a number of subordinate units are spread throughout parallel tributaries that lead off from the main junction. In preferred embodiments, sub units are located at each junction so that for every pipe of branch of piping there is a unit at the entrance to the pipe and a unit at the exit of the pipe. A main unit is situated at the source of the water line and analyses the water composition, which should be the cleanest, at this point. In some scenarios, main units are located at a major juncture that may not be a water source, but rather a starting point that is expected to have high quality water. For the purposes of the present disclosure, a water source is defined as a repository of treated water, whether the water was treated at the instant repository or piped to the repository from another source.

Along the main line, sub-units are deployed in each of the pipes that lead off the main line, and monitor the water make-up at that point. When these secondary lines split off into smaller pipes, the sub-units are located in the smaller pipes. Theoretically, sub-units can be placed at each juncture where a larger volume line splits off into smaller volume lines, although practically, the resolution of the monitoring (i.e. how many sub-units per water system) is dependent on budgets and/or the logistic challenges (pipes size, accessibility etc.).

Each unit includes one or more electro-optic/spectrographic/spectral sensors that monitor the fluid without the use of chemical reactants or reactive agents or the like. The sensor(s) check a number of parameters. For example, spectral sensors (e.g. a photo spectrometer) provide a quantitative measurement of the reflection or transmission properties of a material (molecules in the water) as a function of wavelength. In alternative or additional embodiments, the sensor units include chemical reactants and reagents. The electro-optic and/or chemical based sensors are miniaturized relative to legacy systems and provide cheap, reliable and low-maintenance sensor units. Water in the water supply network is monitored with the sensor units to receive detected sensor values.

The specific way the molecules reflect or transmit light of different wavelengths gives the particular body of water a specific "fingerprint" or "DNA" that can be checked against other bodies of water or the same body of water over time. The "fingerprint", "DNA" or "water profile" is made up of the detected sensor values for a variety of parameters. In embodiments, measurements of additional parameters/characteristics of the water, which are known in the art, are taken by the sensors. In embodiments, water profiles for each water source in area is stored and catalogued in a system database.

Figure 2:
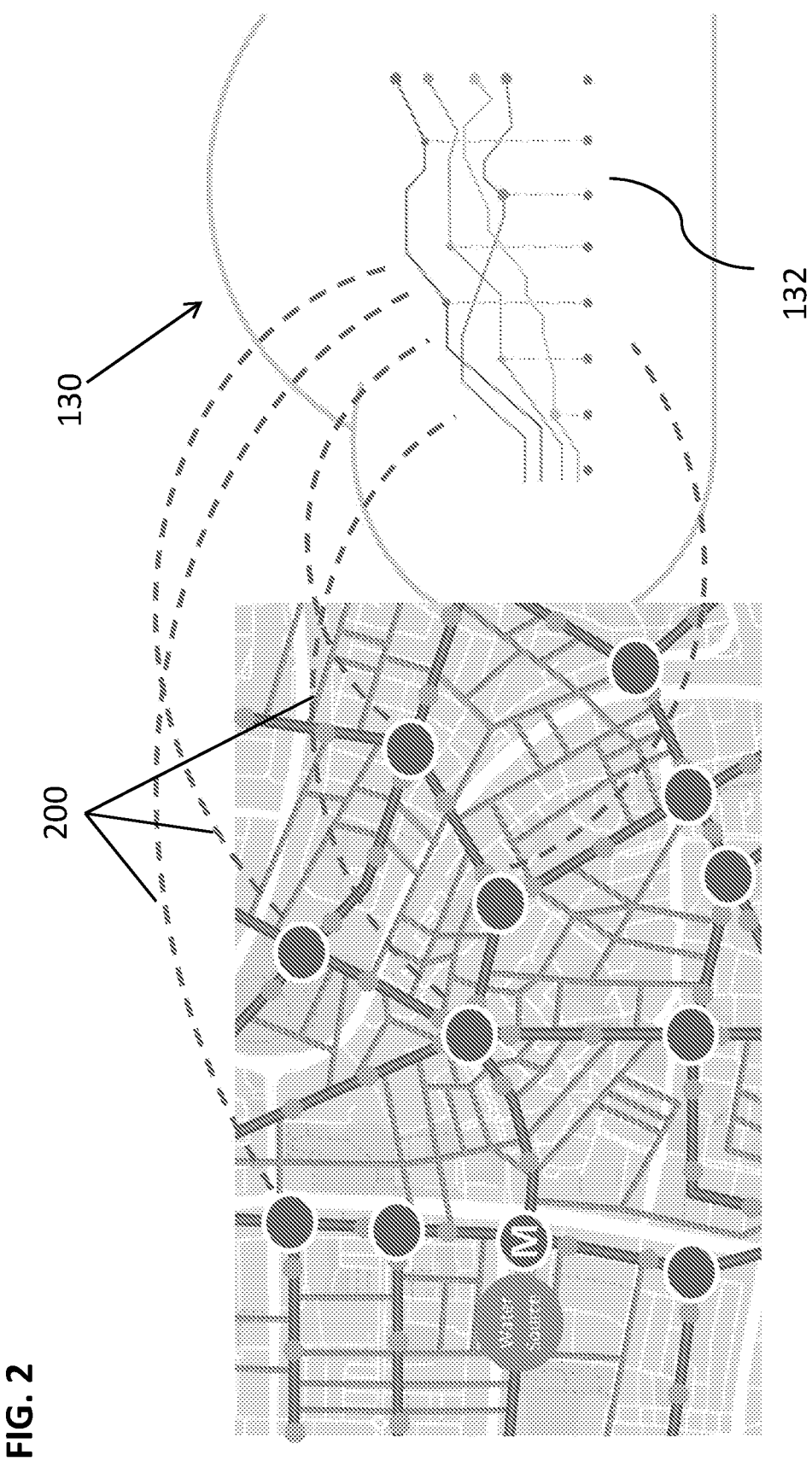
FIG. 2 is a diagram depicting the interconnectivity between the units and the sever computer.

FIG. 2 is a diagram depicting the interconnectivity between the units and the sever computer. The detected sensor values from the plurality of sensor units are communicated 200 to a server computer in real-time or near real-time. To this end, each unit includes a communications component. The communications components may be connected to the server via a wired communications medium, but the components are preferably wireless communications components (partially or entirely) and transmit the monitoring data to a server/cloud server 130. The data is preferably transferred at predefined times, such that the data is all transmitted, periodically, at the same time. It may be necessary to synchronize the local time-clocks of the units periodically, to ensure that the communicated sensor values carry synchronized time stamps. Synchronization may be performed relative to the main unit, or relative to a designated time clock of the cloud server, or relative to a third party source, e.g. a satellite (e.g. GPS) time clock.

The sensor values are received at the server computer and are analyzed 132 in order to detect changes in quality of water moving between the sensor units. The data is processed using algorithms and software to check various parameters. The data from the each individual units is processed, compared and computed, as well as a comparison and computation of the all the data from the other units together.

Figure 7A:
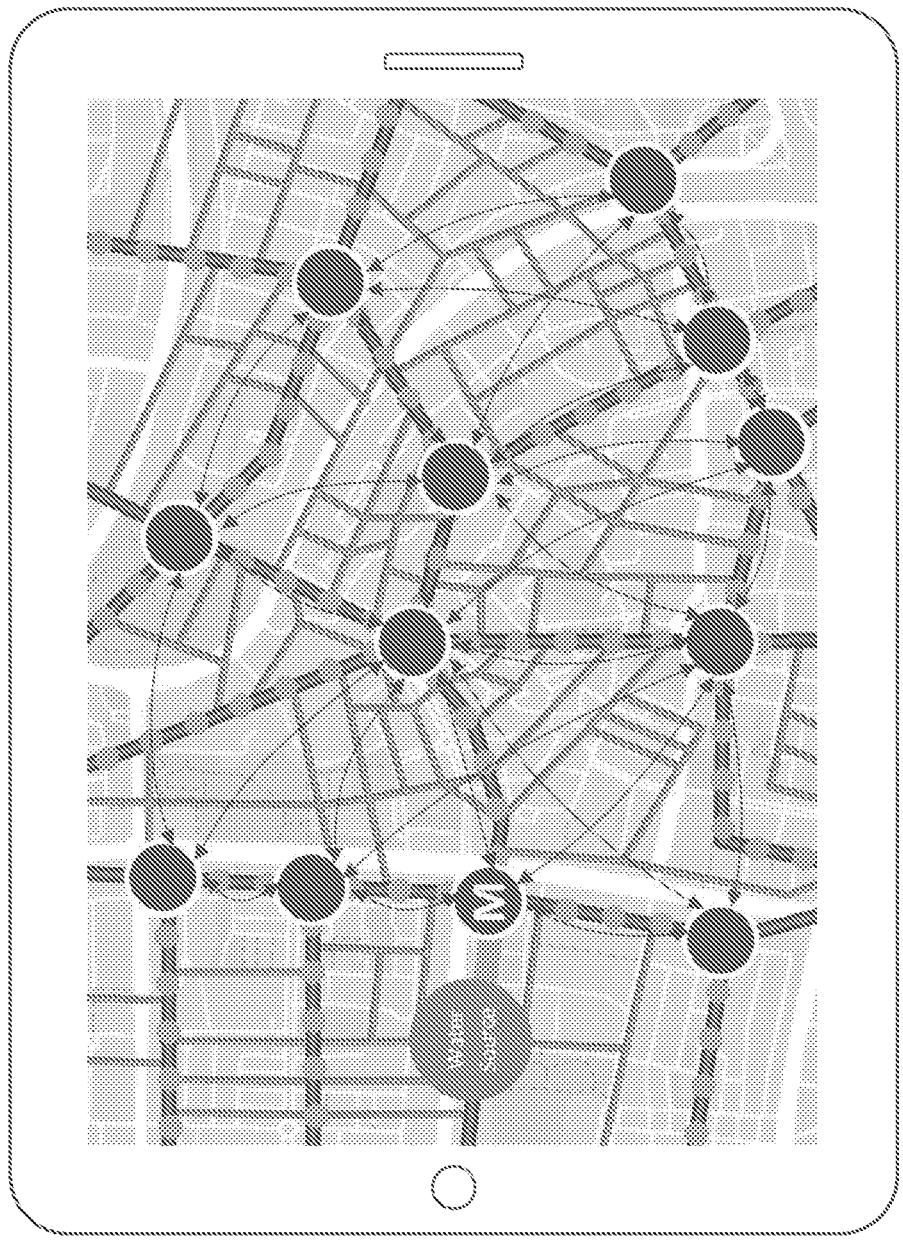
FIG. 7A-7B is a diagrammatic representation of comparisons/cross-referencing between the main unit and the sub units and/or between the sub units themselves.
Figure 7B:
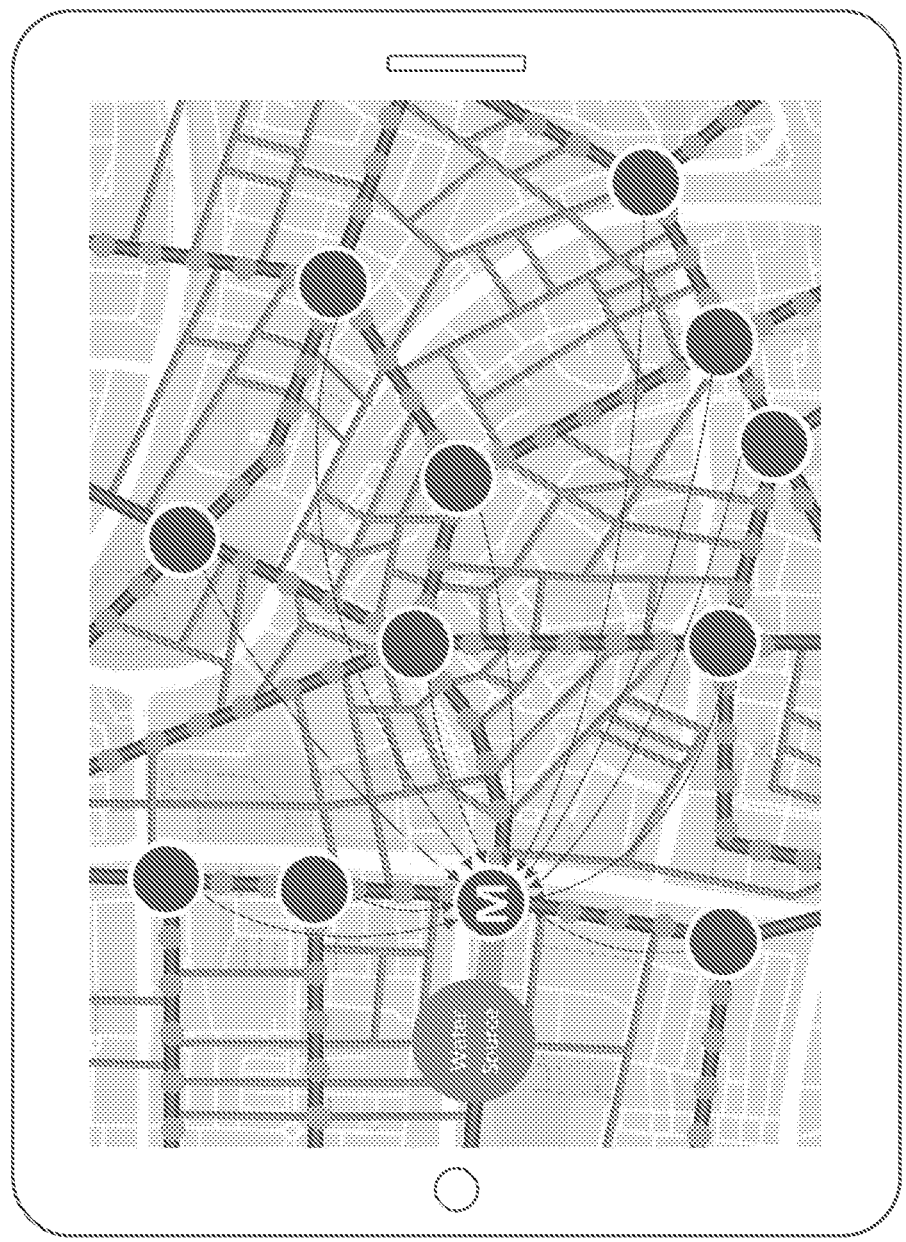

Furthermore, the system on the cloud cross-checks the data collected from the units on the same water line, both between themselves and in relation to the main unit. FIG. 7A depicts a diagrammatic representation of the comparison/cross-referencing between the sub units themselves. The cross referencing may include the main unit and may only be between the sub units. FIG. 7B depicts a diagrammatic representation of the comparison/cross-referencing between the sub units and the main unit. This is done in order to reach a level of optimum accuracy, by identifying even the slightest deviation in relation to the starting point, in order to discover a problem at the earliest stage.

In summary, the system cross-checks online (and in real time), the parameters tested by each unit itself and between the sub-units themselves and in relation to the main unit which serves as a reference point of optimum quality of the water as soon as it enters the line.

Additionally, the server computer records the detected sensor values in a storage repository and compares sensor values from each of the sensor units to recorded values of the same sensor units stored in the repository. In embodiments, sensor values are additionally or alternatively compared/cross-referenced with recorded (historical data) sensor values from other sub units and/or the main unit. Storage facilities, methods of comparison and types of analyses are detailed elsewhere in the document.

Figure 3:
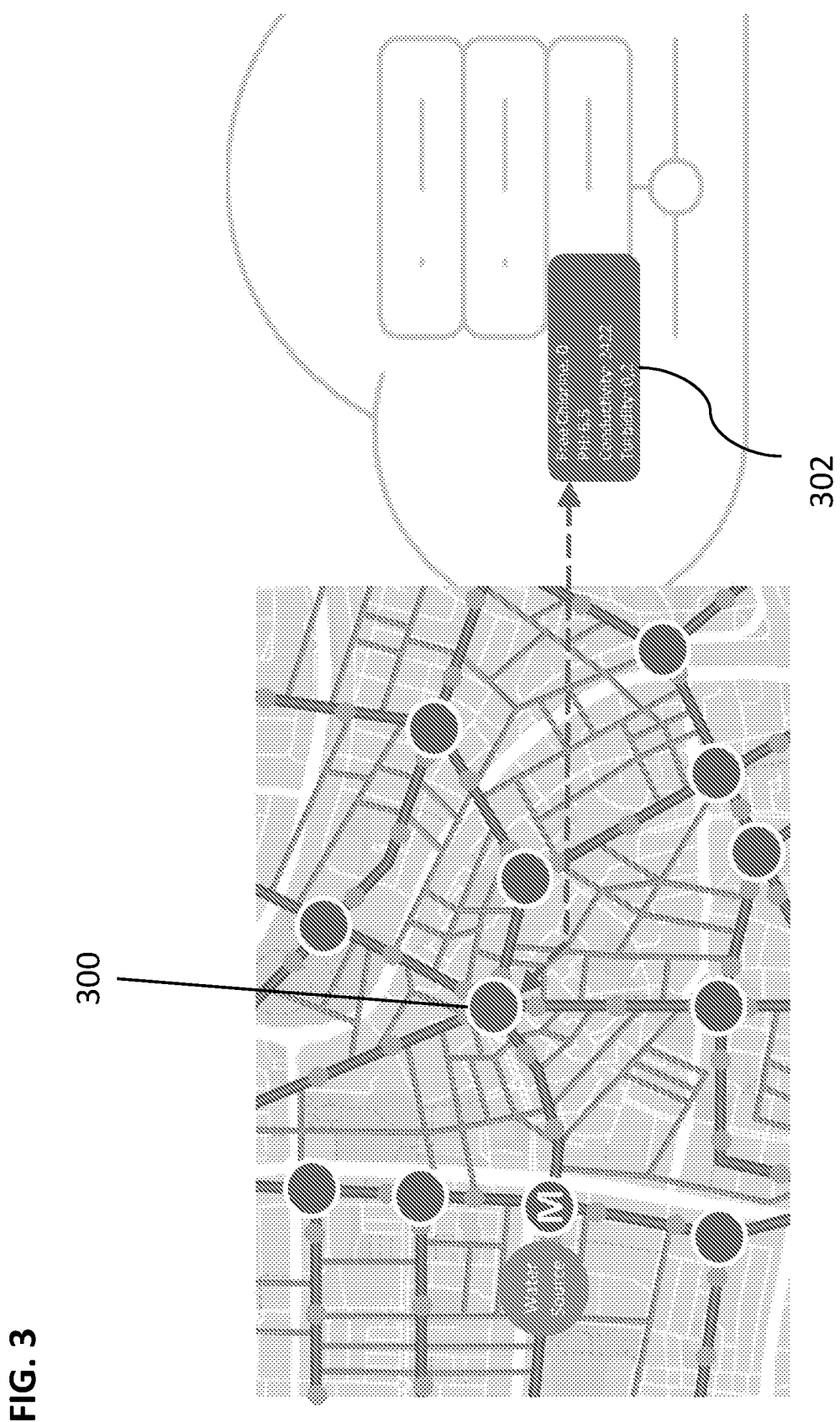
FIG. 3 is an example of a visual notification of a detected anomaly.

FIG. 3 depicts an example of a visual notification of a detected anomaly. When a problem has been discovered, the system notifies the user immediately. The server computer updates the GIS by sending notifications of the detected (and/or calculated) anomalies or malfunctions as well as the locations of these anomalies or malfunctions. The GIS system includes graphic displays of the affected areas and detecting unit 300 in real time (or near real time) by overlaying a digital map with colored indicia which serve to identify both the nature of the problem (based on the color) and the location of the affected areas. For example, unit 300 is displayed in red indicating that location of the detected anomaly and the notification details 302 are depicted in red on the GIS. The color red, exemplarily of course, denotes the level of urgency or contamination that has been depicted at the site. In embodiments, additional or alternative user interfaces are included in the platform. A web-based user interface is provided is provided. The interface can be accessed by a computer browser from both desktop and mobile computing devices, using usernames and passwords etc. A client side computer application and mobile app can be downloaded and installed onto the various computing devices (stationary and mobile) which receives data and interacts with the GIS and/or cloud server. Dedicated terminals and displays may be installed in a command center as well as in other location where the real time or near real-time data is needed. The notifications are embodied in any of graphic, text, audio, visual and/or audio-visual media. In embodiments, the user interface is a Graphic User Interface (GUI) that is not a GIS.

Figure 4:
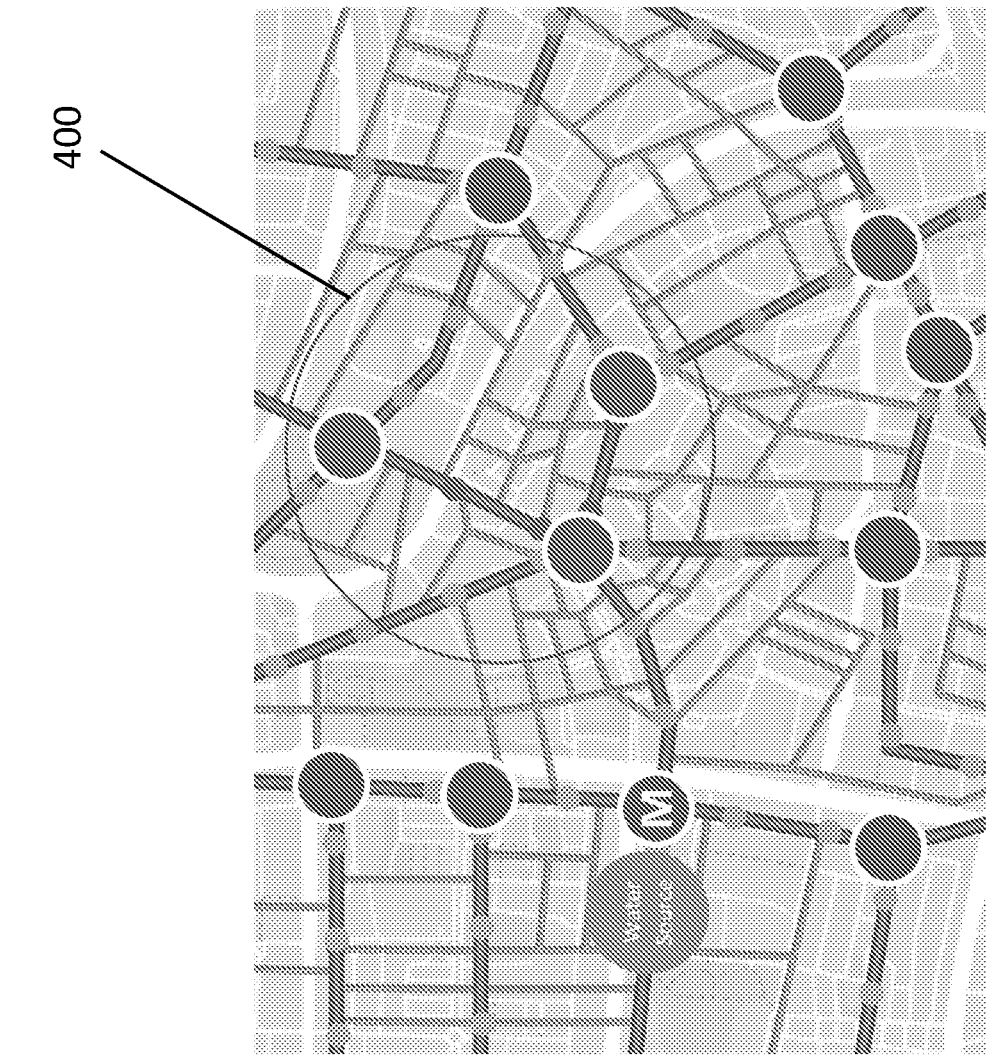
FIG. 4 is an example of a display of a calculated isolation area.

FIG. 4 depicts an example of a display of a calculated isolation area. In embodiments, the system is also programmed to work actively to isolate the affected area. The system detects (or calculates at the cloud server) the rate of water flow and calculates or estimates how far the contamination has spread and seals off the area of the incident 400. In some cases isolation is achieved by automatically closing pipe valves around the area with the contaminated water supply.

In embodiments, an automated purification process is initiated on water in the affected area. Exemplarily, the process may include the automatic introduction of purifying chemicals into the water. Further exemplarily, the process may include activating (e.g. sending a detailed alert) a purification team and supplying the team with data relating to the location of the affected area, the size of the area, various relevant environmental conditions and/or the nature of the contamination. In embodiments, water that has been determined to be contaminated can be manually or automatically flushed from the water supply network.

One of the problems with existing systems is the amount of false positives that monitoring systems receive. The immediate platform includes a plurality of units, many of them placed parallel to each other in adjacent or nearby tributaries that run more or less parallel to the immediate tributary. Hence, alarms received by one unit can be cross-checked with sequential units or randomly selected sub units in the same tributary and/or parallel units in nearby tributaries to determine if the alarm is an anomaly (indicating that the sub-unit may possibly be faulty) or if the alarm is corroborated by subsequent and/or parallel sub-units. As mentioned elsewhere, the sensor values are compared to the sensor values of the main unit.

In embodiments, the cloud server compares communicated sensor values from sequentially located sensor units and sends alerts to the GIS user interface when a localized abnormality is determined at one or more of the sequentially located sensor units relative to other sequentially located sensor units where the abnormality was not detected. The term "sequentially located" units generally refers to sensor units that are located in sequential positions based on water flow direction. Usually water flows in a single direction in any given pipe. However, pipes can diverge in different directions at junctions and in such cases a single direction, a plurality of directions or all directions of water flow can determine which sensor units are sequential, based on the context. Furthermore, the direction of the flow of water can change within the pipe. Also, new water sources can be introduced into a pipe, changing the direction of the flow. The system is capable of sensing direction change as well as identifying the introduction of water from a new water source.

The water system is currently supplied from several sources including: (1) drilling, which includes different types of water and different quality water (2) pumping from open sources, and (3) desalination. Measurements for the same parameters/characteristics tested on these different water-types vary from one type to another. Furthermore, each kind of water-type reacts differently [to the same environment]. The system recognizes the type of water being monitored and analyses the water accordingly, calculating the parameters to correct for the water-type. In embodiments, the server computer (cloud) compares communicated sensor values with predefined sensor value parameters.

As mentioned above, each water source has a specific DNA or "fingerprint". A water profile is created for each water source, defining a set of parameters for the sensor values. Additional water profiles can be created for each of the water sources, where the additional profiles are based on different variables which may apply to the water sources. The water profiles are stored in a system-wide database. As such, the database includes a plurality of predefined sensor value parameters. The profiles may represent the optimal sensor value parameters for a particular location. The profiles may represent the optimal sensor value parameters for a particular location during a given season. The profiles may include relative values between different parameters. For example, if the free chlorine value is equal to X then the PH value will equal Y which is the result of factoring X into a predefined equation for Y.

In embodiments, the water profile for a given water supply network (or a sub-system of the greater network) is dynamically defined. Sensor values collected by the main unit are usually the optimal sensor values, as the main unit is the closest unit to the water purification/treatment center. However, the main unit is also adapted to sense failures or malfunctions in the treatment center, e.g. when the server compares current sensor values from the main unit with historical (recorded) sensor values and identifies an anomaly. In an alternative embodiment, the server identified anomalous readings relative to sub units in the system. The server computer calculates acceptable parameters for the sub-units based on the sensor values of the main unit. Effectively, the computer server compares communicated sensor values from the sub-units to communicated sensor values from the main unit.

Waters are tested extensively to assess how various contaminations manifest in the monitored parameters. Absolute sensor values which are indicative of a contamination are catalogued in the database for each water profile. Relative sensor values, which are indicative of a contamination, are likewise catalogued in the database for each water profile (as each contamination manifests differently in water/fluid from difference sources). Sensor values (absolute and/or relative) for developing contaminations are also catalogued in the database. As a result, the database includes contamination signatures which are values and/or parameters for all the types of manifestations of contaminations or of developing contaminations, for lots of different water profiles. The existing database is constantly updated with new profiles and new parameters as the learning algorithms of the system learn from the ongoing analysis of the sensor data received from the sensor units.

For the purposes of the present document, the term "contamination", with reference to potable water (or other fluid in a useful state), refers to water (or other fluid) that has been altered from a state in which the water was deemed useable. The contamination may be a minor contamination that does not render the water unusable or the contamination may be a major alteration which renders the water unfit for use.

"Contamination signature" is a term used to refer to a combination of factors that indicate that water in the system has been contaminated. A contamination signature is similar to a computer virus signature (from where the term is borrowed) in that virus detection software searches for virus signatures when scanning files. The signatures are the telltale signs in the code that indicate to the software that the code is malware. Using virus signatures as a linguistic allegory, contamination signatures are sets of absolute or relative sensor values that indicate that the water is contaminated.

As discussed above the contamination signatures (absolute or relative sensor values indicative of a contamination or an evolving/developing contamination) are stored and catalogued in the server computer database. Detection of one of the contamination signatures in the water network results in an alert being sent to the GIS. In embodiments, contamination signatures are based on relative values between parameters of free chlorine, PH, turbidity and conductivity. In embodiments, contamination signatures are based on given (absolute) values of one or more: a free chlorine value, a PH value, a turbidity value and a conductivity value. In embodiments, contamination signatures can be based on measurements of additional parameters/characteristics of the water, which are known in the art to indicate water quality.

Figure 5:
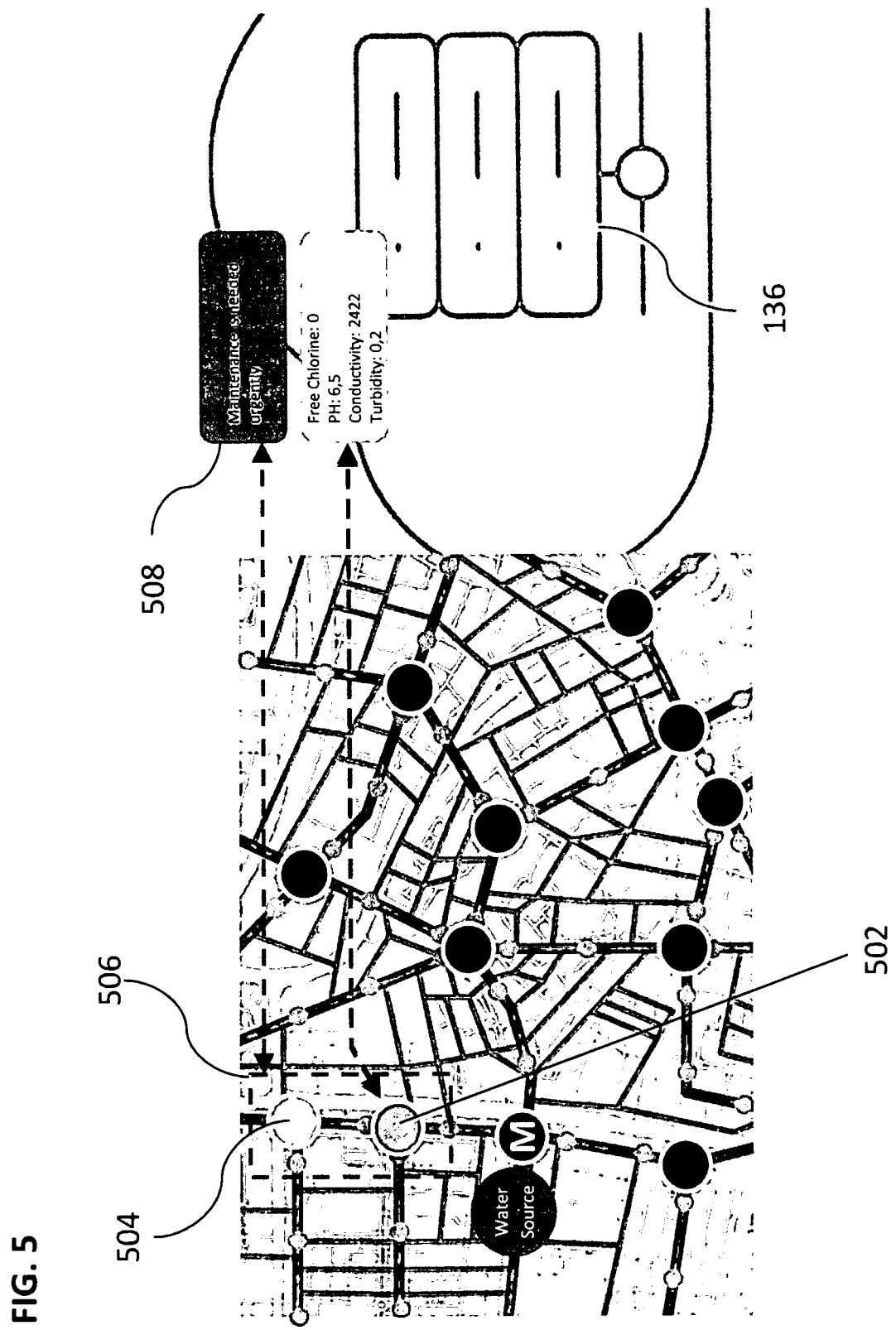
FIG. 5 is an example of a graphic display of an evolving anomaly in a localized area.

FIG. 5 depicts an example of a graphic display of an evolving anomaly in a localized area. The system collects all the ongoing, incoming data from the field and includes learning algorithms 136 that know and/or learn how to recognize usual behavior that differs from normal scenarios observed over time and analyzes the behavior in order to learn to skip over data that creates false positives. For example, slow degradation of a particular pipe or group of pipes can result in the system flagging many false positives. The system learns that the sensor values, compared over time, indicate a degradation, malfunction or impending malfunction and provides the appropriate notifications and alerts. The server computer sends alerts or notifications to the GIS when the communicated sensor values are found to be outside the predefined parameters. An exemplary graphic display on the GIS is shown in FIG. 5. Sensor readings differ between one unit 502 and another unit 504 indicating immediately, or over time, that within a definable segment 506 of the network an maintenance issue has been detected. The graphic display indicates the units in a different color (e.g. yellow, indicating a need for maintenance) and sends and displays a text notification 508 on the GIS.

Figure 6:
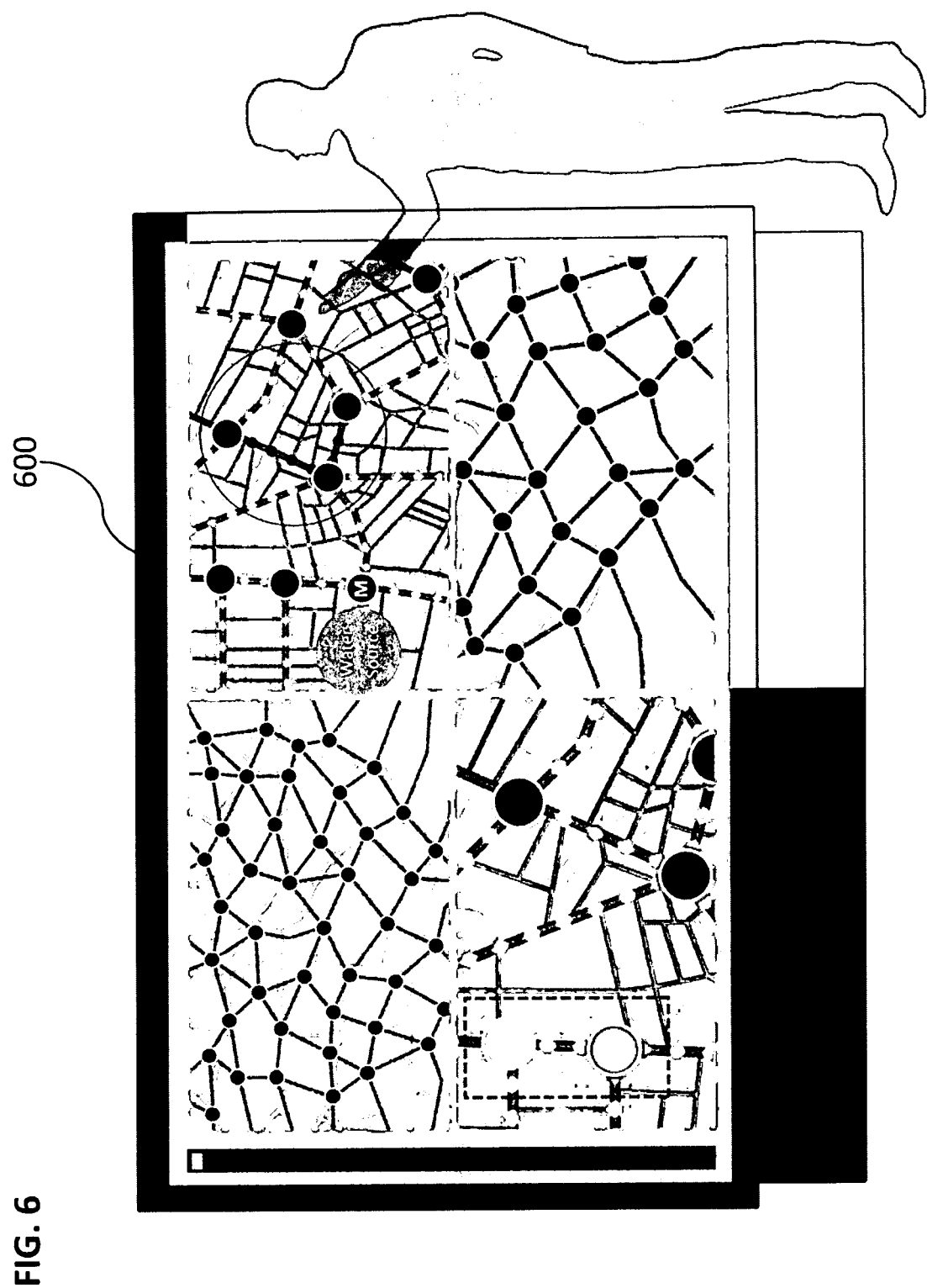
FIG. 6 is an exemplary graphic display of the system.

FIG. 6 depicts an exemplary graphic display of the system. In preferred embodiments, the GIS is embodied both on a multimedia display 600 in a command center as well as on stationary terminals (e.g. desktop computers) and mobile terminals (laptops, tablet computers, smartphones, navigation device) and on a web interface that can be accessed by personnel. The GIS is an exemplary embodiment. It is made clear that the system may be embodied on a GUI or even a text (e.g. SMS, email, Whatsapp™ and/or other messenger services) system or an audio system.

As mentioned, some contamination signatures are detectable over time. As such, recorded values are analyzed and compared to the contamination signatures in the database. If a match is found, then an alert is sent. In some cases a prediction of a future match can also be made, resulting in a similar notification.

Due to the fact that the system is composed of a large number of units—up to even thousands of units in each sector—and in order to reduce and optimize the system maintenance, the sub-units of the system can be calibrated remotely, by manual calibration of the main unit. Once the main unit is properly calibrated (e.g. on a regular basis or during a periodic maintenance overhaul), the main unit sends out calibration commands to all the sub-units that relate back to the main unit. The sub-units automatically recalibrate/reset according to the calibration parameters of the main unit.

To create consistent control over the accuracy of the sensors, the system performs cross-checks of the sensors in the following configuration: each sensor type test will be performed laterally on all sensors of the same main/subordinate cluster, in order to isolate and identify whether the fault is a sensor malfunction instead of a problem with the water. The assumption is that when there is a contamination it is supposed to affect more than one parameter in the water and therefore other sensor values should also reflect a problem with the water.

If the problem is with a particular sensor in a sensor unit then the sensor values output by that sensor should be different to other sensors in the same tributary (in sequentially located units). Furthermore, the rest of the parameters detected by the entire unit should be within the healthy ranges and congruent with the same sensor readings in other units. Thus, indicating that the problem is with the specific sensor in the specific unit. When there is a problem with the water, it is likely that more than one unit will detect the problem, and therefore abnormal sensor values will be outputted from more than one unit. If there is a failure or malfunction with an entire unit, then all the sensor values should be incongruent with the values from the sequential sensors, the parallel sensors (sensors in similar positions along parallel tributaries) or both. In embodiments, a calibration fluid is permanently stored in each sensor unit which recalibrates the sensors is a malfunction is detected. The calibration liquid has set values/characteristics to which each of the sensors is supposed to react in the same way. When one or more of the sensors returns unexpected or "incorrect" values then that is an indication the there is an irregularity with the sensor(s).

When a malfunction is determined (of a sensor or an entire unit), a notification is sent to the GIS. One manner of dealing with a malfunction is to remotely reset or recalibrate the sensor or unit. Alternatively or additionally, the server automatically corrects the readings taking into consideration the detected deviation. If the problem persists a maintenance team may be dispatched to physically fix the sensor/unit or replace the sensor/unit.

Sensors

Each sensor unit (whether a main unit or a sub unit) is housed in a box or container which contains a variety of sensors. At least one section of the container may be transparent for optical sensors to transmit and receive optical pulses which analyze the fluid. In addition to the sensors that have been mentioned previously, the device may further include one or more of the following sensors:

(a) Turbidity sensor
    (b) Chlorine detection sensor
    (c) PH sensors
    (d) EC—Electricity conduct sensors
    (e) TSS—sensors
    (f) UV absorption sensors
    (g) (k) ORP sensor
    (h) No2 Sensor
    (i) No3 Sensor
    (j) NH4+ sensor
    (k) $O_2$ sensor Light emitting or light detecting sensors (multi wave lengths) include:

(a) IR sensor
    (b) Optical sensors—Prismatic sensor
    (c) An internal light source—of various light wave lengths
    (d) And/or any other applicable sensors, in the casing of the device.

The sensor units may be installed on/in the pipe or replace a segment of the pipe or "look" at the water through a "window" or opaque glass or any other transparent material chosen and through which the fluid test will be carried out by the various sensors.

According to embodiments, some tests may require pumping of the water or fluid into a small storage tank (within the housing or adjacent to the housing) where a more in-depth analysis of fluid can be made while the water is static, instead of in motion, in order to obtain more accurate data where types of tests require exposure to the fluid for more exhaustive examination by the sensors.

At the end of the test, the fluid will be pumped back into the pipe as it has not been used for any purpose except that it was removed from the flow cycle for a very short period of time. The reintroduction of monitored water is possible because the sensor units comprise passive sensors only. No reactants or reagents are introduced into the water or any other type of intervention that changes the chemical and biological makeup of the water. In other embodiments, the water samples are invasively tested (e.g. as described above), such that the samples cannot be returned to the supply network. In such cases, the samples sizes are very small (e.g. a pico-liter or a little more) and the amount of chemicals employed proportionately reduced (resulting in a huge saving of money). The samples may be stored in a storage tank (which is periodically vacated) or flushed outside the pipes.

One of the paradigm shifts presented by the present innovative system is to change the perception from protecting only the water facilities, to also protecting the water itself.

Figure 8:
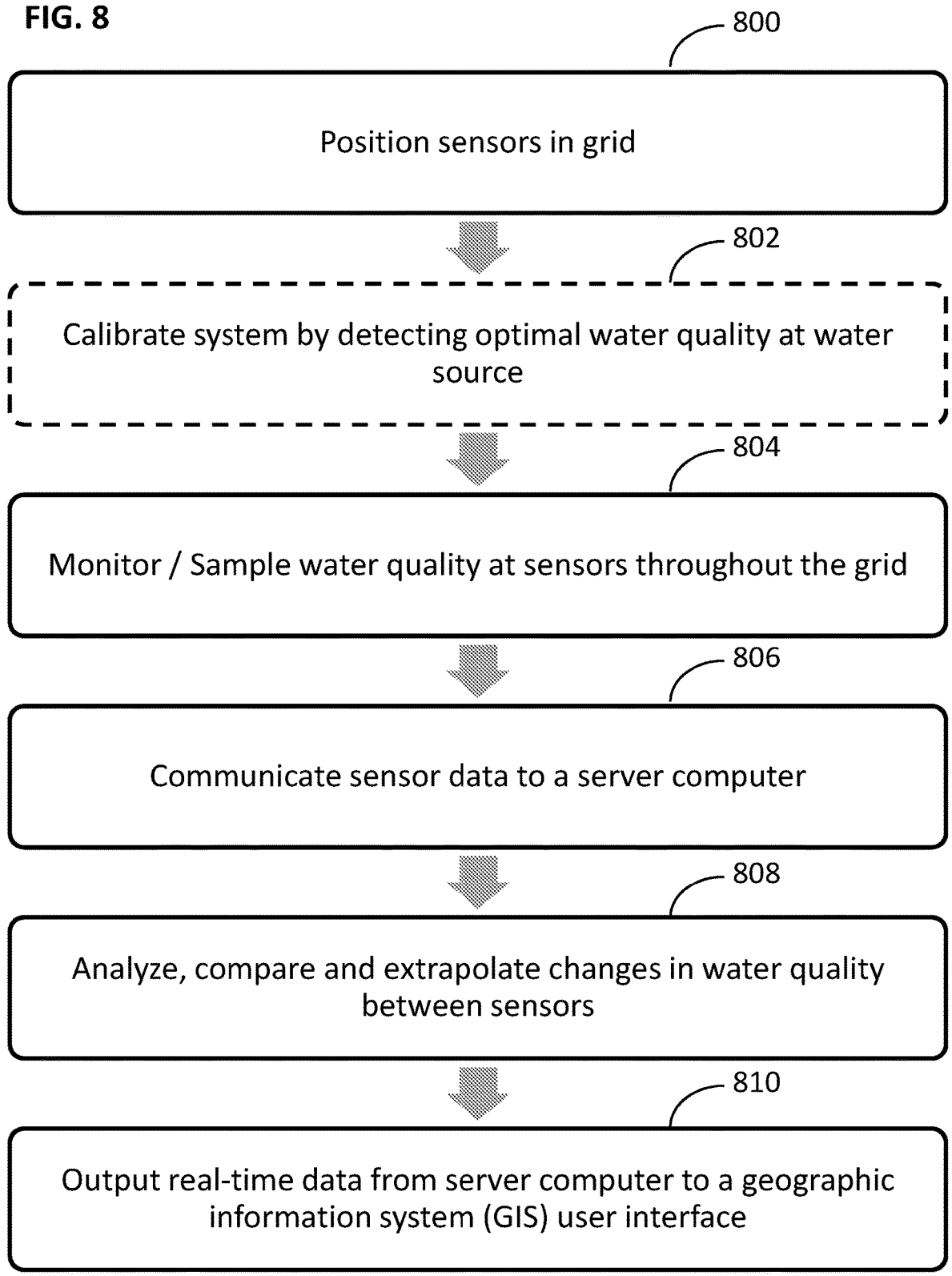
FIG. 8 is a flow diagram of a method and process for monitoring water quality in a water supply network.

An embodiment of the present innovative method and process for monitoring water quality in a water supply network is depicted in the flow diagram in FIG. 8.

At step 800 a plurality of sensor units are provided at predefined locations along the water supply network. The plurality of sensor units includes a main unit and sub-units.

More than one cluster (main and sub units) can be positioned in the same water supply network, effectively delineating a sub network within the main network. For the purposes of the present disclosure, each such sub network is considered a network in itself. The main unit is positioned near an outlet from a water treatment plant, ensuring that the optimal water is scanned by the sensors, and the resulting sensor values serve as base-line parameters for the sub units. In embodiments, the sub units are positioned sequentially moving away from the main unit to the end points of the network. In preferred embodiments, the sub units are located at each juncture within the network, as described above.

In embodiments, the sub units are calibrated based on the sensor values from the main unit, at step 802.

At step 804 water is monitored (or sampled and returned to the system, as described above) by the network of sensor units throughout the water supply network.

Step 806 includes communicating detected sensor values from the plurality of sensor units to a server computer in real-time. The term server computer (and variations thereof) is used to refer equally to a dedicated server, a server farm with distributed processing and storage capabilities between the collocated devices and a cloud server(s).

At the server, in step 808, the sensor values are analyzed in order to monitor the health level of the water and detect changes in the health and quality of water moving between the sensor units.

At step 810 real-time (or near real-time) data from the server computer is outputted to a geographic information system (GIS) user interface. The outputted data includes a visual depiction of the supply network including color-coded indicia which indicate the health level of the water in the depicted locations. The outputted data includes audio notifications and alerts, as well as recorded messages. The outputted data includes text-based information. The audio, visual, audio-visual, text and other notifications can be provided on any of a plurality of media including: the digital map/grid in a command center, computer terminals, mobile computing devices (e.g. tables, smartphones, laptops etc.). Notifications can be in the form of emails, push notifications, audio alarms, recorded audio messages, SMS messages, location data compatible with navigation applications, and any type of analogue and/or digital messages communicated via the Internet, cellular communications, satellite communications, wired and wireless means, RF-based communications and any other types of communication medium known in the art.

Figure 9:
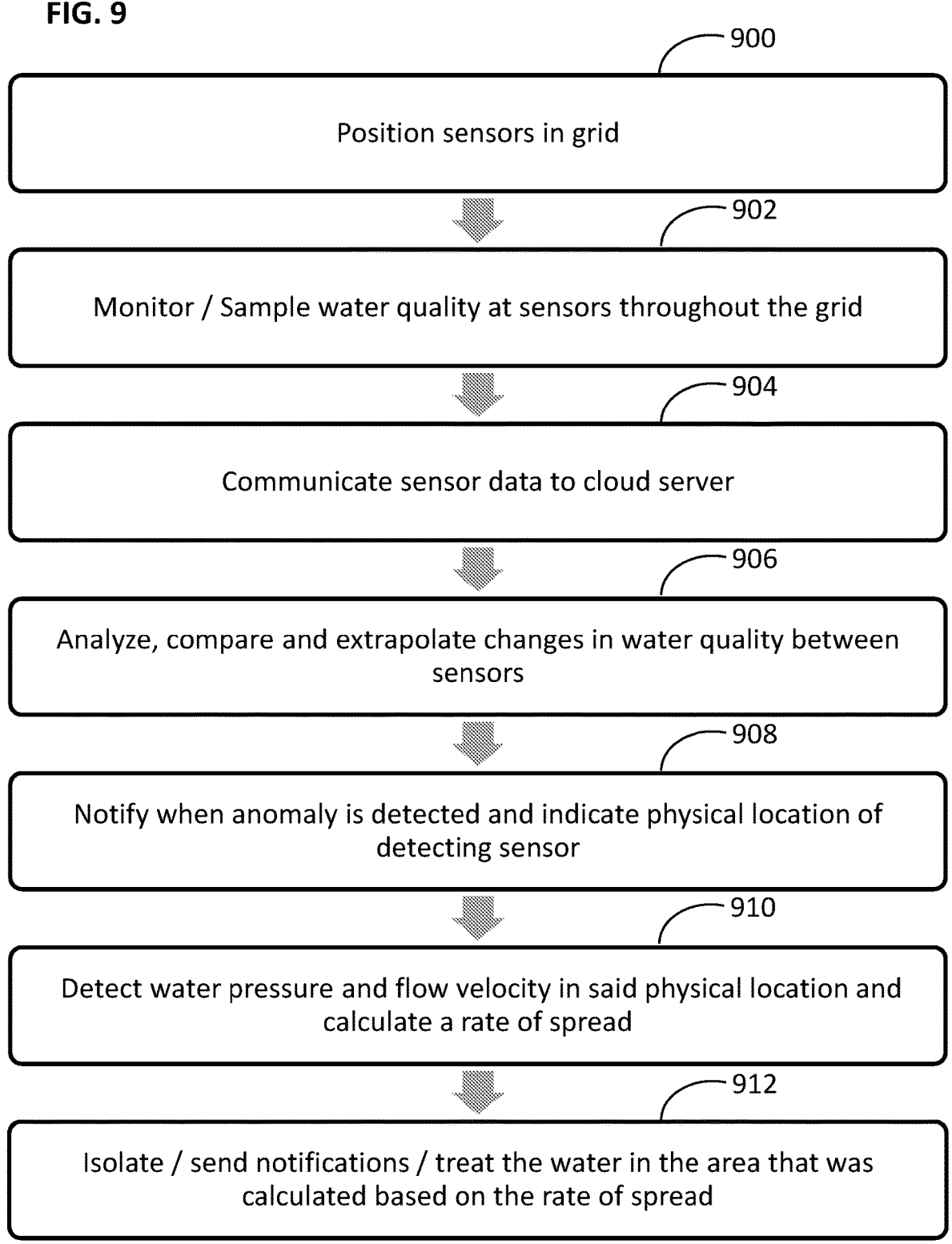
FIG. 9 is a flow diagram of an embodiment of a method and process for monitoring water quality in a water supply network.

An embodiment of the present innovative method and process for monitoring water quality in a water supply network is depicted in the flow diagram in FIG. 9.

At step 900 the sensor units are positioned in the grid. At step 902 the water quality is measured and monitored throughout the water system, based on predefined and/or dynamically defined (or dynamically refined) characteristics, parameters and value ranges. At step 904 the sensor values are communicated (in a wired or wireless manner, as described in further detail above) to the server computer (cloud server). This communication happens at predetermined intervals on a consistent basis.

At step 906 the sensor values/data is processed by the processing facility of the cloud server to analyze, compare and extrapolate changes in water quality between sensor units.

Data processing is well known in the art and can be implemented in a myriad of ways. The term "processing facility" refers any and all hardware, firmware and software necessary for performing any manner of data processing needed for the tasks detailed herein. A partial list of the aforementioned includes one or more processors [CPU, microprocessor, ASIP, GPU, PPU, DSP coprocessor, floating-point unit, network processor, multi-core processor, front-end processor, etc.], memory [volatile and non-volatile: RAM, DRAM, SRAM, ROM, PROM, EPROM, EEPROM, solid state storage, flash memory, movable headed hard drives, magnetic tape, optical disc drives etc.], software, algorithms, machine learning logic, artificial intelligence and more.

At step 908 the system detects or identifies an anomaly (or developing anomaly, malfunction or failure) and the physical location of the detecting sensor unit. The processing facility sends notifications of the anomalies or malfunctions, including locations thereof, to the GIS user interface. Anomalous occurrences include, but are not limited to, pipe degradation, new or chronic failures in the treatment facility, human error, malfunction of chemical dispensers, sewerage seepage, introduction of bacteria and other biological agents due to natural disasters, accidents, illicit human intervention and the like.

At step 910 the system detects water pressure and flow velocity in the physical location and calculates a rate of spread of the water from the sensor unit or units that detected the anomaly. At step 912 one or more of the following actions are taken on the area calculated to contain the contaminated water: (a) sending an alert including an indication of the affected area for maintenance crews to be dispatched to the location; (b) automatically isolating the affected area by closing automated valves in the water system or sending instructions to water network administrators to do so; (c) effecting an automated purification process on water in the affected area; and (d) flushing water in the affected area from the water supply network.

Figure 10:
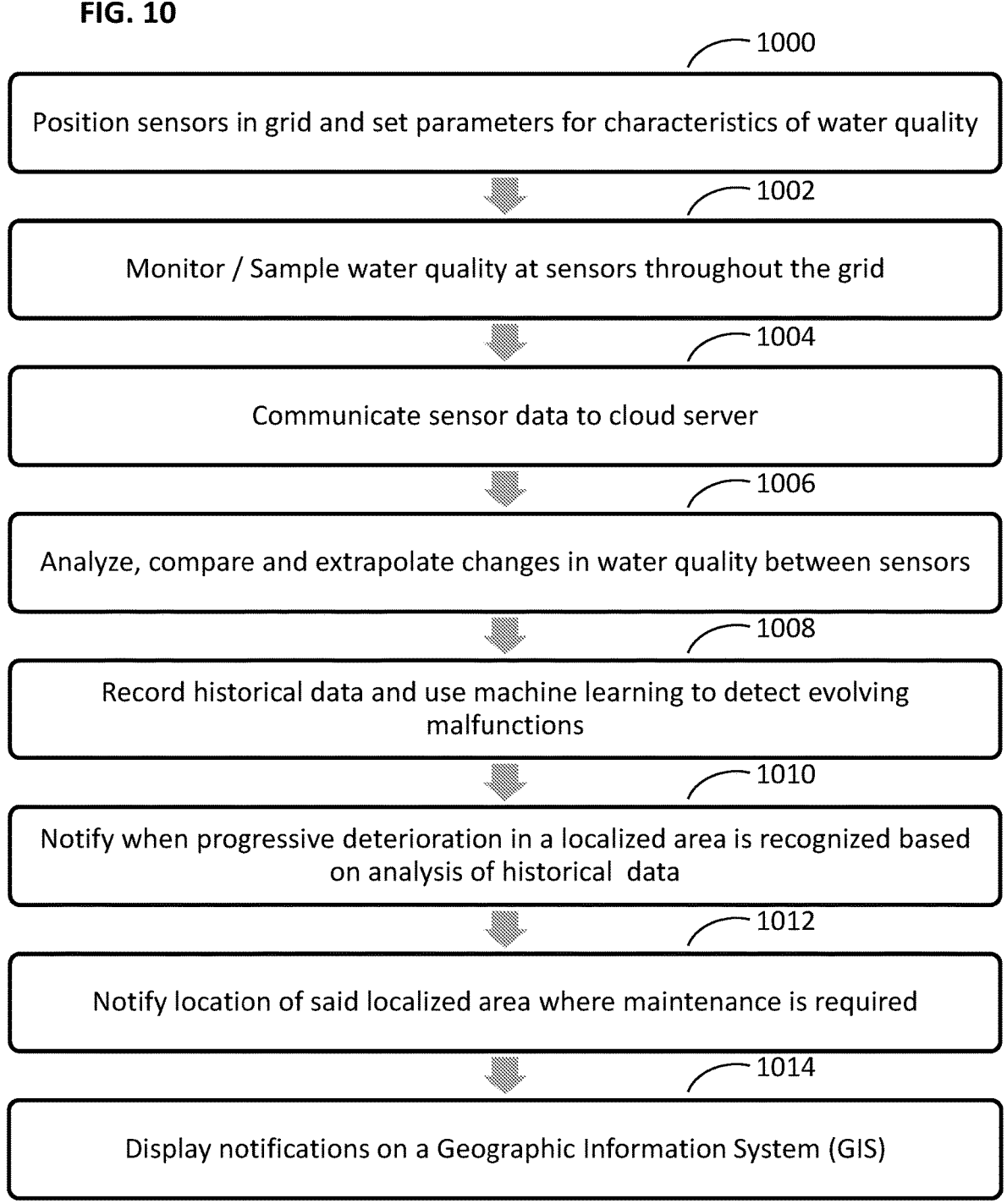
FIG. 10 is a flow diagram of an embodiment of a method and process for monitoring water quality in a water supply network.

An embodiment of the present innovative method and process for monitoring water quality in a water supply network is depicted in the flow diagram in FIG. 10.

At step 1000 the sensor units are positioned in the grid. At step 1002 the water quality is measured and monitored throughout the water system, based on predefined and/or dynamically defined (or dynamically refined) characteristics, parameters and value ranges. At step 1004 the sensor values are communicated to the server computer. This communication happens at predetermined intervals on a consistent basis.

At step 1006 the sensor values/data is processed by the processing facility of the cloud server to analyze, compare and extrapolate changes in water quality between sensor units.

At step 1008, the server computer records the detected sensor values in a storage repository. As part of the analysis, the server compares sensor values from each of the plurality of sensor units to recorded values of the same sensor units stored in the repository. While the term "repository" may lend itself to interpretation of a single device, it is made clear that the storage facility intended by the term repository can be a single storage device, multiple linked storage devices that are collocated, cloud storage or any other manner or mechanism for storing digital data.

By using the recorded historical data and machine learning the system is able to detect evolving anomalous occurrence. Anomalous occurrences include, but are not limited to, pipe degradation, new or chronic failures in the treatment facility, human error, sewerage seepage, introduction of bacteria and other biological agents due to natural disasters, accidents, illicit human intervention and the like.

Slowly evolving occurrences (e.g. pipe degradation which results in the slow release of contaminants into the water at a progressively rate) cause two problems for legacy monitoring systems: non-detection of the problem and, conversely, many false positives (resulting in false alarms and a tendency to ignore the problematic readings). The gradual contamination raises some flags in the system but the overall picture, at any given time, is that there is no problematic contamination.

The present innovative data processing system analyzes water from a historical perspective, comparing data from the same sensors over time, which allows the systems and processors to identify developing anomalies before they become outright malfunctions, failures, contaminations or a combination thereof.

At step 1010 the system sends notifications to and via the GIS UI when progressive deterioration in a localized area is recognized based on analysis of historical data.

At step 1012 the system notifies the UI of the location of the localized area where maintenance is required.

At step 1014 the notifications are displayed on a Geographic Information System (GIS) in a command center. Additionally or alternatively, the display and other manner of notification are sent to terminals which may be stationary terminals or mobile terminals. Maintenances crews can be dispatched to perform the necessary maintenance and can be guided by mobile terminals (navigation devices, tablet computers, smart phones, etc.) to the appropriate locations.

Some of the steps in the aforementioned processes may be skipped or realized in a different order than the order in which the steps are presented. Furthermore, some of the various processes that have been described with reference to FIGS. 8, 9 and 10 include steps or details that have been omitted when describing other processes. It is the express intent that the steps described heretofore are exemplarily and can be interchanged with steps from other processes, added to some processes and/or omitted from other processes. The processes are not intended to be limiting but rather to demonstrate preferred embodiments of the innovative system.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A method for monitoring water quality in a water supply network, the method comprising:
providing a plurality of sensor units at a plurality of predefined locations, each sensor unit of said plurality of sensor units located at a corresponding location of said plurality of predefined locations along the water supply network;
providing a database of a plurality of water source profiles;
detecting a first estimated flow rate and direction between sequential units of said plurality of sensor units from water pressure data;
for said each sensor unit of said plurality of sensor units, generating a detected value indicative of a parameter of the water quality at said corresponding location;
communicating said detected value from to a computer server in real-time;
analyzing by said computer server of said detected value indicative of said parameter of the water quality for estimating a mixture of said water source profiles at said corresponding location;
determining a second estimated flow rate and direction from the mixture of said water source profiles at said corresponding location;
identifying a contamination source based on changes in said water quality of water moving between said plurality of predefined locations and said first estimated flow rate and said second estimated flow rate;
storing calibration fluid at least one of said plurality of predefined locations; and
remotely recalibrating said each sensor unit of said plurality of sensor units using said calibration fluid, and
wherein said identifying the contamination source includes identifying an unmeasured contaminant by comparing, by said computer server, of said detected value at said plurality of predefined locations over time to a contamination signature.

2. The method of claim 1, wherein said analyzing includes a change over time in said detected value.

3. The method of claim 1, wherein said generating is of values of at least two different parameters and said analyzing is based on relative values between said at least two different parameters.

4. The method of claim 3 wherein said at least two different parameters are selected from a set consisting of values of free chlorine, PH, turbidity value, a Total suspended solids (TSS) value, a Ultraviolet (UV) absorption value, an oxidation-reduction potential (ORP) value, a two oxygen (O2) concentration value and conductivity.

5. The method of claim 1, wherein said analyzing is based on said detected value of at least one of: a free chlorine value, a PH value, a turbidity value, a Total suspended solids (TSS) value, a Ultraviolet (UV) absorption value, an oxidation-reduction potential (ORP) value, a two oxygen (O2) concentration value and a conductivity value.

6. The method of claim 1, further comprising: outputting said changes in said water quality in t real-time from said computer server to a geographic information system (GIS) user interface or a Graphic User Interface (GUI).

7. The method of claim 1, wherein said estimating the mixture of said water source profiles at a given location is based on said detected sensor value for each of a plurality of parameters at an upstream location.

8. The method of claim 1, wherein said estimating the mixture of said water source profiles at a given location is based on flow data and said detected sensor value for each of a variety of parameters at a plurality of said predefined locations.

9. The method of claim 8, wherein said flow data includes data on more than one water source into the water supply network.

10. A method for monitoring water quality in a water supply network, the method comprising:
providing a plurality of sensor units, each sensor unit of said plurality of sensor units located at a corresponding location of a plurality of predefined locations along the water supply network;
providing a database including a plurality of contamination signatures;
each contamination signature of said plurality of contamination signatures associating a time dependent set of sensor values with a type of contamination and a water type of a plurality of types of contaminations and a plurality of water types;

for said each sensor unit of said plurality of sensor units generating a detected value indicative of a parameter of the water quality at said corresponding location;

communicating said detected value to a computer server in real-time;

estimating, by said computer server, of rates and directions of flow between said plurality of predefined locations; and further analyzing, by said computer server, said detected value in order to detect changes in the water quality of a water moving between said plurality of predefined locations; and identifying a contamination event and an unmeasured type of contaminant by comparing, by said computer server, of said detected value over time to said plurality of contamination signatures; and sending a contamination alert reporting said contamination event and said unmeasured type of contaminant to a user interface in response to said identifying, and wherein said estimating is from flow measurements, and wherein said computer server includes the database of a plurality of water source profiles and the method further comprising:

said analyzing by said computer server of said detected value indicative of the parameter of the water quality for estimating a mixture of said water source profiles at said corresponding location;

determining a second estimated flow rate and direction from the mixture of said water source profiles at said corresponding location; and calibrating said rates and directions of the flow between said plurality of predefined locations using said second estimated flow rate and direction by said computer server.

11. The method of claim 10, further comprising:
learning by said computer server to adjust said plurality of contamination signatures when said contamination alert is false.

12. The method of claim 10, further comprising: analyzing historical records of a water parameter to identify a slowly developing anomaly; recognizing said slowly developing anomaly as a sign of a progressive deterioration in a local area; and wherein said sending the contamination alert reporting said contamination event includes an alert of said progressive deterioration and a location of said local area.

13. The method of claim 12, further comprising:
calculating an affected area based on a rate of spread of h water from said local area, and effecting at least one of: sending said alert including an indication of said affected area, automatically isolating said affected area by sealing off said affected area, sending instructions to water network administrators, effecting an automated purification process on the water in said affected area, and flushing the water in said affected area from the water supply network.

14. The method of claim 10, wherein said identifying is based on relative values between parameters of free chlorine, PH, turbidity and conductivity.

15. The method of claim 10, wherein said identifying is based on predefined values of at least one of: a free chlorine value, a PH value, a turbidity value and a conductivity value.

16. The method of claim 10, wherein at least one of said plurality of contamination signatures is based on relative values between at least two parameters.

17. The method of claim 16, wherein said at least two parameters are selected from a set consisting of values of free chlorine, PH, turbidity value, a Total suspended solids (TSS) value, a Ultraviolet (UV) absorption value, an oxidation-reduction potential (ORP) value, a two oxygen (O2) concentration value and conductivity.

18. The method of claim 10, wherein said plurality of contamination signatures are based on predefined values of at least one of a free chlorine value, a PH value, a turbidity value, a Total suspended solids (TSS) value, a Ultraviolet (UV) absorption value, an oxidation-reduction potential (ORP) value, a two oxygen (O2) concentration value and conductivity.

* * * * *